United States Patent
Megerian et al.

(10) Patent No.: US 11,289,203 B2
(45) Date of Patent: Mar. 29, 2022

(54) CUSTOMIZED AGGREGATE SCORING USING MACHINE LEARNING

(71) Applicant: International Business Machines Corporation, Armonk, NY (US)

(72) Inventors: Mark Gregory Megerian, Rochester, MN (US); Thomas J Eggebraaten, Rochester, MN (US); Marie Louise Setnes, Bloomington, MN (US); John Petri, St. Charles, MN (US)

(73) Assignee: International Business Machines Corporation, Armonk, NY (US)

( * ) Notice: Subject to any disclaimer, the term of this patent is extended or adjusted under 35 U.S.C. 154(b) by 124 days.

(21) Appl. No.: 16/283,902

(22) Filed: Feb. 25, 2019

(65) Prior Publication Data

US 2020/0273571 A1 Aug. 27, 2020

(51) Int. Cl.
*G16H 50/20* (2018.01)
*G06F 3/0482* (2013.01)

(52) U.S. Cl.
CPC .......... *G16H 50/20* (2018.01); *G06F 3/0482* (2013.01)

(58) Field of Classification Search
CPC .............................. G16H 50/20; G06F 3/0482
USPC .......................................................... 705/2
See application file for complete search history.

(56) References Cited

U.S. PATENT DOCUMENTS

| | | | |
|---|---|---|---|
| 8,706,519 B2 | 4/2014 | Gliklich | |
| 10,431,339 B1* | 10/2019 | Cornelius | G16H 10/60 |
| 2011/0202361 A1* | 8/2011 | Firminger | G06Q 40/08 |
| | | | 705/2 |
| 2012/0016690 A1* | 1/2012 | Ramarajan | G16H 15/00 |
| | | | 705/2 |
| 2012/0047105 A1 | 2/2012 | Saigal et al. | |
| 2016/0224760 A1* | 8/2016 | Petak | G16H 50/20 |
| 2017/0076046 A1 | 3/2017 | Barnes et al. | |
| 2018/0199815 A1* | 7/2018 | Redei | G16H 80/00 |
| 2019/0311810 A1* | 10/2019 | Sevenster | G06Q 50/22 |
| 2019/0362846 A1* | 11/2019 | Vodencarevic | G16H 50/30 |
| 2020/0227172 A1* | 7/2020 | Perkins | G16H 20/30 |

OTHER PUBLICATIONS

Broekhuizen, Henk et al. "Estimating the value of medical treatments to patients using probabilistic multi criteria decision analysis." BMC medical informatics and decision making vol. 15 102. Dec. 2, 2015, doi: 10.1186/s12911-015-0225-8 (Year: 2015).*

* cited by examiner

*Primary Examiner* — Christopher L Gilligan
*Assistant Examiner* — Bennett Stephen Erickson
(74) *Attorney, Agent, or Firm* — Patterson + Sheridan, LLP

(57) ABSTRACT

A computing system receives a plurality of medical perspectives for each medical treatment option of a plurality of medical treatment options. A machine learning model assigns a weight to each medical perspective for each medical treatment option by determining how often a care provider has agreed with each perspective within the plurality of medical perspectives. The computing system receives a medical treatment option ranking for each of the medical perspectives. The computing system generates a score for each medical perspective as applied to each medical treatment option based on a combination of the weight and the ranking for each medical perspective. The computing system aggregates the scores across the plurality of medical perspectives into an overall score for each medical treatment option.

20 Claims, 12 Drawing Sheets

| Therapy Name | Institution Specific Recommendations | Consensus Guidelines | Published Literature | Adverse Reactions | Relative Cost |
|---|---|---|---|---|---|
| Carboplatin | Not Recommended | Uniform, Low | 1 Result | 52 | X |
| Carboplatin / paclitaxel | Not Recommended | Uniform, Low | 2 Results | 82 | W |
| Carboplatin / paclitaxel / bevacizumab | Acceptable | Uniform, Low | 2 Results | 107 | Y |
| Cisplatin | Not Recommended | Uniform, Low | 6 Results | 24 | Y |
| Cisplatin / gemcitabine | Not Recommended | | 2 Result | 44 | X |
| Cisplatin / paclitaxel | Not Recommended | Uniform, High | 5 Results | 72 | X |
| Cisplatin / paclitaxel / bevacizumab | Preferred | Uniform, High | 1 Result | 107 | Y |
| Cisplatin / topotecan | Not Recommended | Uniform, Low | 3 Results | 30 | X |
| Paclitaxel | Not Recommended | Uniform, Low | 1 Result | 69 | W |
| Topotecan / paclitaxel | Not Recommended | Uniform, Low | 1 Result | 69 | X |
| Topotecan / paclitaxel / bevacizumab | Acceptable | Uniform, High | 1 Result | 107 | Z |

FIG. 3A

| Institution Specific Recommendations | Consensus Guidelines | Published Literature | Adverse Reactions | Relative Cost |
|---|---|---|---|---|
| Cancer Type - Cervical Cancer | Cancer Type - Cervical Cancer | Cancer Type - Cervical Cancer | Cancer Type - Cervical Cancer | Cancer Type - Cervical Cancer |
| Age - 40 | FIGO Stage - IVB | Prior Therapies - None | | |
| Overall Health - Symptomatic, Fully Ambulatory | Amenable to Local Treatment - No | Histology - Adenosquamous Carcinosarcoma | | |
| Prior Therapies - None | | Overhall Health - Symptomatic Fully Ambulatory | | |
| FIGO Stage - IVB | | FIGO Stage - IVB | | |
| Staging Workup - PET | | Age - 40 | | |
| Recurrence - None | | | | |
| Histology - Adenosquamous Carcinoma | | | | |

FIG. 3B

| Institution Specific Recommendations (1) | Consensus Guidelines (2) | Published Literature (5) | Adverse Reactions (4) | Relative Cost (3) |
|---|---|---|---|---|
| 90% | 72% | 29% | 39% | 61% |

FIG. 3C

| Therapy Name | Institution Specific Recommendations | Consensus Guidelines | Published Literature | Adverse Reactions | Relative Cost |
|---|---|---|---|---|---|
| Carboplatin | (3) Not Recommended | (2) Uniform, Low | (5) 1 Result | (4) 52 | (2) X |
| Carboplatin / paclitaxel | (3) Not Recommended | (2) Uniform, Low | (4) 2 Results | (7) 82 | (1) W |
| Carboplatin / paclitaxel / bevacizumab | (2) Acceptable | (2) Uniform, Low | (4) 2 Results | (8) 107 | (3) Y |
| Cisplatin | (3) Not Recommended | (2) Uniform, Low | (1) 6 Results | (1) 24 | (3) Y |
| Cisplatin / gemcitabine | (3) Not Recommended | | (4) 2 Result | (3) 44 | (2) X |
| Cisplatin / paclitaxel | (3) Not Recommended | (1) Uniform, High | (2) 5 Results | (6) 72 | (2) X |
| Cisplatin / paclitaxel / bevacizumab | (1) Preferred | (1) Uniform, High | (5) 1 Result | (8) 107 | (3) Y |
| Cisplatin / topotecan | (3) Not Recommended | (2) Uniform, Low | (3) 3 Results | (2) 30 | (2) X |
| Paclitaxel | (3) Not Recommended | (2) Uniform, Low | (5) 1 Result | (5) 69 | (1) W |
| Topotecan Paclitaxel | (3) Not Recommended | (2) Uniform, Low | (5) 1 Result | (5) 69 | (2) X |
| Topotecan / paclitaxel / bevacizumab | (2) Acceptable | (1) Uniform, High | (5) 1 Result | (8) 107 | (4) Z |

FIG. 3D

| Therapy Name | Institution Specific Recommendations | Consensus Guidelines | Published Literature | Adverse Reactions | Relative Cost |
|---|---|---|---|---|---|
| Carboplatin | (33)*(90)=2970 | (50)*(72)=3600 | (20)*(29)=580 | (25)*(39)=975 | (50)*(61)=3050 |
| Carboplatin / paclitaxel | (33)*(90)=2970 | (50)*(72)=3600 | (25)*(29)=725 | (14)*(39)=546 | (100)*(61)=6100 |
| Carboplatin / paclitaxel / bevacizumab | (50)*(90)=4500 | (50)*(72)=3600 | (25)*(29)=725 | (13)*(39)=507 | (33)*(61)=2013 |
| Cisplatin | (33)*(90)=2970 | (50)*(72)=3600 | (100)*(29)=2900 | (100)*(39)=3900 | (33)*(61)=2013 |
| Cisplatin / gemcitabine | (33)*(90)=2970 | | (25)*(29)=725 | (33)*(39)=1287 | (50)*(61)=3050 |
| Cisplatin / paclitaxel | (33)*(90)=2970 | (100)*(72)=7200 | (50)*(29)=1450 | (17)*(39)=663 | (50)*(61)=3050 |
| Cisplatin / paclitaxel / bevacizumab | (100)*(90)=9000 | (100)*(72)=7200 | (20)*(29)=580 | (13)*(39)=507 | (33)*(61)=2013 |
| Cisplatin / topotecan | (33)*(90)=2970 | (50)*(72)=3600 | (33)*(29)=957 | (50)*(39)=1950 | (50)*(61)=3050 |
| Paclitaxel | (33)*(90)=2970 | (50)*(72)=3600 | (20)*(29)=580 | (20)*(39)=780 | (100)*(61)=6100 |
| Topotecan Paclitaxel | (33)*(90)=2970 | (50)*(72)=3600 | (20)*(29)=580 | (20)*(39)=780 | (50)*(61)=3050 |
| Topotecan / paclitaxel / bevacizumab | (50)*(90)=4500 | (100)*(72)=7200 | (20)*(29)=580 | (13)*(39)=507 | (25)*(61)=1525 |

FIG. 3E

| Therapy Name | Institution Specific Recommendations | Consensus Guidelines | Published Literature | Adverse Reactions | Relative Cost | [Average] |
|---|---|---|---|---|---|---|
| Carboplatin | 2970 | 3600 | 580 | 975 | 3050 | 2235 |
| Carboplatin / paclitaxel | 2970 | 3600 | 725 | 546 | 6100 | 2788.2 |
| Carboplatin / paclitaxel / bevacizumab | 4500 | 3600 | 725 | 507 | 2013 | 2269 |
| Cisplatin | 2970 | 3600 | 2900 | 3900 | 2013 | 3076.6 |
| Cisplatin / gemcitabine | 2970 | 7200 | 725 | 1287 | 3050 | 2008 |
| Cisplatin / paclitaxel | 2970 | 7200 | 1450 | 663 | 3050 | 3066.6 |
| Cisplatin / paclitaxel / bevacizumab | 9000 | 7200 | 580 | 507 | 2013 | 3860 |
| Cisplatin / topotecan | 2970 | 3600 | 957 | 1950 | 3050 | 2505.4 |
| Paclitaxel | 2970 | 3600 | 580 | 780 | 6100 | 2806 |
| Topotecan Paclitaxel | 2970 | 3600 | 580 | 780 | 3050 | 2196 |
| Topotecan / paclitaxel / bevacizumab | 4500 | 7200 | 580 | 507 | 1525 | 2862.4 |

FIG. 3F

| Therapy Name | Institution Specific Recommendations | Consensus Guidelines | Relative Cost | Adverse Reactions | Published Literature |
|---|---|---|---|---|---|
| Carboplatin | (33)*(90)=2970 | (50)*(72)=3600 | (50)*(61)=3050 | (25)*(39)=975 | (20)*(29)=580 |
| Carboplatin / paclitaxel | (33)*(90)=2970 | (50)*(72)=3600 | (100)*(61)=6100 | (14)*(39)=546 | (25)*(29)=725 |
| Carboplatin / paclitaxel / bevacizumab | (50)*(90)=4500 | (50)*(72)=3600 | (33)*(61)=2013 | (13)*(39)=507 | (25)*(29)=725 |
| Cisplatin | (33)*(90)=2970 | (50)*(72)=3600 | (33)*(61)=2013 | (100)*(39)=3900 | (100)*(29)=2900 |
| Cisplatin / gemcitabine | (33)*(90)=2970 | | (50)*(61)=3050 | (33)*(39)=1287 | (25)*(29)=725 |
| Cisplatin / paclitaxel | (33)*(90)=2970 | (100)*(72)=7200 | (50)*(61)=3050 | (17)*(39)=663 | (50)*(29)=1450 |
| Cisplatin / paclitaxel / bevacizumab | (100)*(90)=9000 | (100)*(72)=7200 | (33)*(61)=2013 | (13)*(39)=507 | (20)*(29)=580 |
| Cisplatin / topotecan | (33)*(90)=2970 | (50)*(72)=3600 | (50)*(61)=3050 | (50)*(39)=1950 | (33)*(29)=957 |
| Paclitaxel | (33)*(90)=2970 | (50)*(72)=3600 | (100)*(61)=6100 | (20)*(39)=780 | (20)*(29)=580 |
| Topotecan Paclitaxel | (33)*(90)=2970 | (50)*(72)=3600 | (50)*(61)=3050 | (20)*(39)=780 | (20)*(29)=580 |
| Topotecan / paclitaxel / bevacizumab | (50)*(90)=4500 | (100)*(72)=7200 | (25)*(61)=1525 | (13)*(39)=507 | (20)*(29)=580 |

FIG. 3G

| Therapy Name | Institution Specific Recommendations | Consensus Guidelines | Relative Cost | Adverse Reactions | Published Literature | [Average] |
|---|---|---|---|---|---|---|
| (6) Carboplatin | 2970 | 3600 | 3050 | 975 | 580 | 3206.667 |
| (4) Carboplatin / paclitaxel | 2970 | 3600 | 6100 | 546 | 725 | 4223.333 |
| (5) Carboplatin / paclitaxel / bevacizumab | 4500 | 3600 | 2013 | 507 | 725 | 3371 |
| (8) Cisplatin | 2970 | 3600 | 2013 | 3900 | 2900 | 2861 |
| (7) Cisplatin / gemcitabine | 2970 | 3600 | 3050 | 1287 | 725 | 3010 |
| (3) Cisplatin / paclitaxel | 2970 | 7200 | 3050 | 663 | 1450 | 4406.667 |
| (1) Cisplatin / paclitaxel / bevacizumab | 9000 | 7200 | 2013 | 507 | 580 | 6071 |
| (6) Cisplatin / topotecan | 2970 | 3600 | 3050 | 1950 | 957 | 3206.667 |
| (4) Paclitaxel | 2970 | 3600 | 6100 | 780 | 580 | 4223.33 |
| (6) Topotecan Paclitaxel | 2970 | 3600 | 3050 | 780 | 580 | 3206.667 |
| (2) Topotecan / paclitaxel / bevacizumab | 4500 | 7200 | 1525 | 507 | 580 | 4408.333 |

FIG. 3H

CUSTOMIZED AGGREGATE SCORING USING MACHINE LEARNING

BACKGROUND

The present invention relates to aggregate scoring of medical treatment recommendations, and more specifically, to dynamically weighting various medical perspectives for a particular patient based on the learned preferences of a health care provider.

In existing systems for ranking medical treatment options, the medical treatment options are ranked separately based on multiple, isolated medical perspectives. Existing systems do not provide a mechanism for reconciling the recommendations across multiple medical perspectives. Many medical care providers have preferred medical perspectives or place differing trust in each of the medical perspectives. Existing system further do not provide rankings of medical perspectives that take into account care provider preferences. Further, particular attributes of respective medical perspectives may be useful for ranking medical treatment options and for providing treatment recommendation, but existing systems fail to account for particular attributes of respective medical perspectives when ranking each treatment or for providing treatment recommendations.

SUMMARY

According to one embodiment of the present invention, a computing system receives a plurality of medical perspectives for each medical treatment option of a plurality of medical treatment options for a medical disorder. Each of the plurality of medical perspectives provides an independent view for evaluating the plurality of medical treatment options for treating the medical disorder. A machine learning model implemented by the computing system assigns a weight to each of the plurality of medical perspectives for each of the plurality of medical treatment options by determining how often a care provider agrees with the plurality of medical perspectives based on historical medical treatment option selections made by the care provider. The computing system receives a medical treatment option ranking for each of the plurality of medical perspectives. Each medical treatment option ranking is based on how a corresponding one of the plurality of medical perspectives grades each of the plurality of medical treatment options. The computing system generates a score for each medical perspective of the plurality of medical perspectives as applied to each medical treatment option of the plurality of medical treatment options based on a combination of the weight and the ranking for each medical perspective. The computing system aggregates the scores across the plurality of medical perspectives into an overall score for each of the plurality of medical treatment options independent of the plurality of medical perspectives.

BRIEF DESCRIPTION OF THE SEVERAL VIEWS OF THE DRAWINGS

FIGS. 3A-3H show one example of a sequence of displays that lead to providing an aggregate score for medical treatment options.

DETAILED DESCRIPTION

Figure 1:
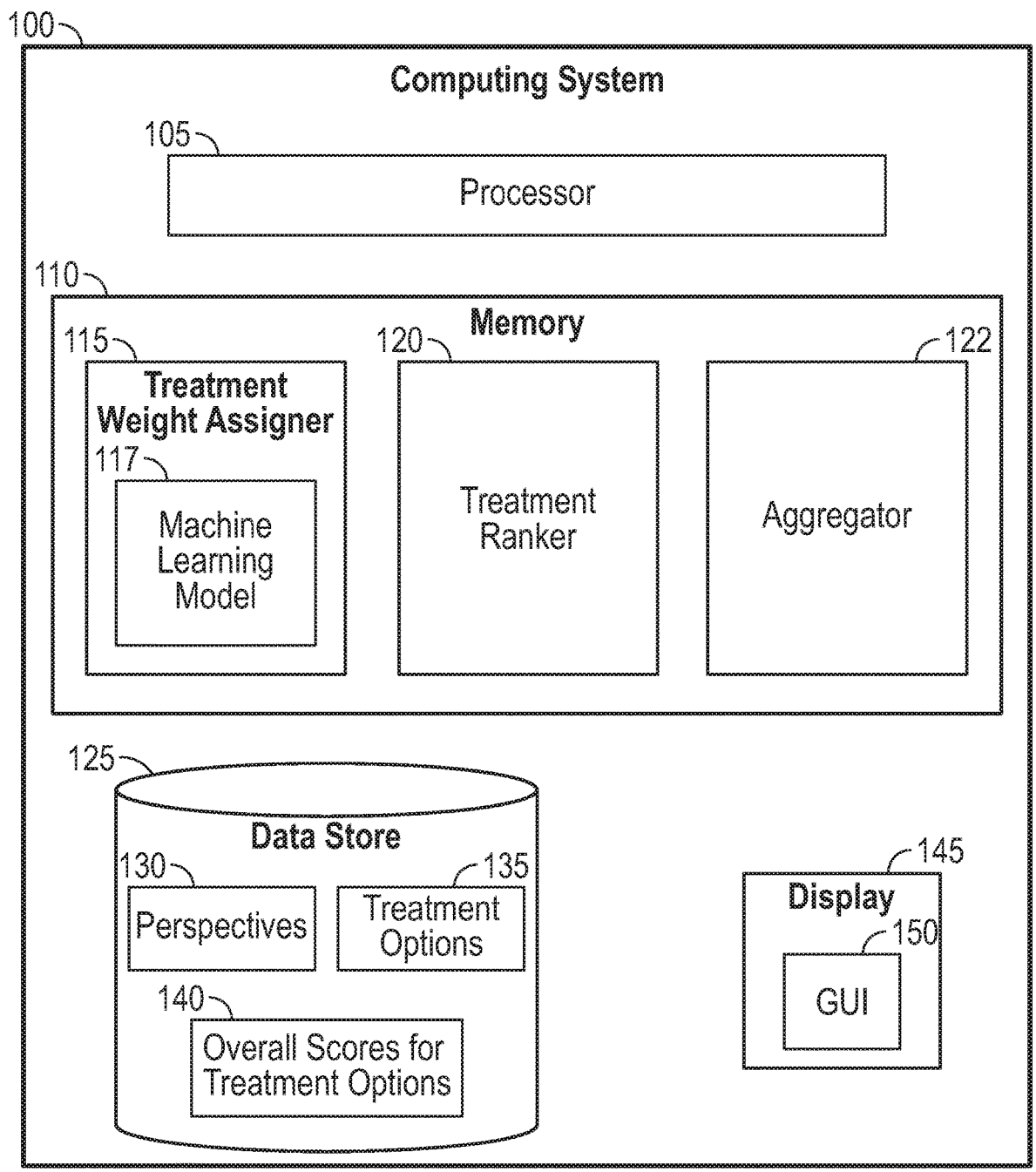
FIG. 1 illustrates a computing system for providing an aggregate score for medical treatment options, according to one embodiment described herein.

Embodiments of the present disclosure provide a system and method that provides an aggregate score for medical treatment options. In particular, embodiments can dynamically weight various medical perspectives for a particular patient based on learned preferences of a health care provider. The medical treatment options and medical perspectives are ranked, aggregated, and displayed in a GUI of a display associated with the system. The GUI provides an interface for the care provider to view and provide input for altering the ranking of each medical treatment option. The GUI is the interface through which health care providers can view medical treatment options for a particular patient across a variety of sources/medical perspectives (different guidelines, institutional practices, computer-provided recommendations based on a review of the relevant literature, etc.). Each of these sources can potentially consider a different set of patient attributes in formulating a medical perspective (e.g., computer-provided methods may consider 40 patient attributes, while a given treatment guideline may only consider 5 patient attributes). The system can provide medical treatment selections for medical treatment options for particular patients over time, and can track how frequently the doctor/health care provider tends to agree with the recommendations of various medical perspectives.

The system can learn how a physician's/institution's treatment selections tend to align with the recommendations of various medical perspectives, and can assign weights to the medical perspectives accordingly. That is, rather than simply changing the GUI, the system changes the execution flow of a machine learning method to provide more weight for medical perspectives the health care provider relies on, and less weight to the medical perspectives that the health care provider rarely uses. For example, a given physician's historical treatment selections may align with the recommendations of national cancer guidelines, expert institution practice, and real world evidence. These medical perspectives are then assigned high weights when generating the aggregate scores for each medical treatment option and for each medical perspective. Similarly, the physician's treatment selections may not align with the expense of the treatment (e.g., the physician frequently does not select the least expensive treatment). These medical perspectives would therefore be accorded low weight.

The weights for the various medical perspectives for calculating an aggregate score of a medical treatment option can be dynamic and can depend on the preferences/learned history of the health care provider. The system can further reorganize the data displayed in the GUI to prioritize different preferences (e.g., the most preferred medical perspective is displayed in the left most column, the 2nd most preferred medical perspective is displayed in the 2nd to left column, etc.). Lower priority medical perspectives can be removed from the GUI altogether, and can be replaced with more preferred medical perspectives that previously were not displayed.

Thus, not only does the data for medical treatment options change based on the health care provider (or institution), but the rankings of the medical perspectives can be updated to reflect the health care provider's (or institution's) methodologies. Moreover, when calculating an aggregate score for each medical treatment option, the system can weigh the recommendations of the various medical perspectives using the aforementioned weights, thereby tailoring the overall recommendations to the learned preferences of the physician.

As used herein, a medical perspective provides an independent view for evaluating a plurality of medical treatment options for treating a medical disorder. A medical perspective originates from one of a medical treatment guideline, a practice of an institutional, a computer-provided recommendation based on a review of relevant literature, a number of reported adverse effects for each medical treatment option in the medical perspective, and a cost of the medical treatment option.

Medical perspectives may originate from a machine-learning model, in which ranking is performed using machine learning. Other medical perspectives may originate from hospital databases including the most popular treatment, most commonly given treatment, or has the fewest reported adverse events. Embodiments of the present disclosure can combine the aforementioned types of medical perspectives to provide a meta-analysis of multiple medical perspectives to provide a customized aggregate score that takes into account the different types of medical perspectives.

While the present disclosure focuses on medical perspective aggregation of medical treatment options, other embodiments may focus on perspective aggregation of other types of perspectives of other knowledge realms. For example, a maintenance technician may be presented with a GUI that shows several action plans for troubleshooting a nonconformance in a device or structure (e.g., an air conditioner, a building, a computer, a vehicle) and several paradigms (e.g., a manufacturer's recommendation, a company policy, previous technician's notes) that recommend one action plan over another action plan. In this embodiment, action plans are evaluated across perspectives of the action plans.

FIG. 1 illustrates a computing system 100 for providing an aggregate score for medical treatment options, according to one embodiment described herein. The computing system 100 includes a processor 105, (main) memory 110, and a persistent data store 125. The processor 105 constructs a treatment weight assigner 115 which includes a machine learning model 117, a treatment ranker 120, and an aggregator 122 by fetching instructions of a program stored in the data store 125 and loading the treatment weight assigner 115 including the machine learning model 117, the treatment ranker 120, and the aggregator 122 into the main memory 110. The processor 105 represents one or more processing elements that each may include multiple processing cores. The treatment weight assigner 115 generates a graphical user interface (GUI) 150 on a display 145. The GUI 150 displays a plurality of medical perspectives 130a-130n. Each respective medical perspective (e.g., 130i) of the plurality of medical perspectives 130a-130n is used to evaluate a plurality of medical treatment options 135a-135n. The treatment weight assigner 115 assigns a plurality of weights to each of the plurality of medical perspectives 130a-130n for each of the plurality of medical treatment options 135a-135n. Each weight is reflective of a preference for each of the plurality of medical perspectives 130a-130n by a care provider. The treatment ranker 120 generates a score for each of the plurality of medical perspectives 130a-130n for each of the plurality of medical treatment options 135a-135n based on the assigned plurality of weights. The aggregator 122 aggregates the score for each medical perspective (e.g., 130i) of the plurality of medical perspectives 130a-130n for each medical treatment option (e.g., 135i) of the plurality of medical treatment options (135a-135n) into an overall score for each medical treatment option (e.g., 135i) of the plurality of medical treatment options (135a-135n).

Figure 2:
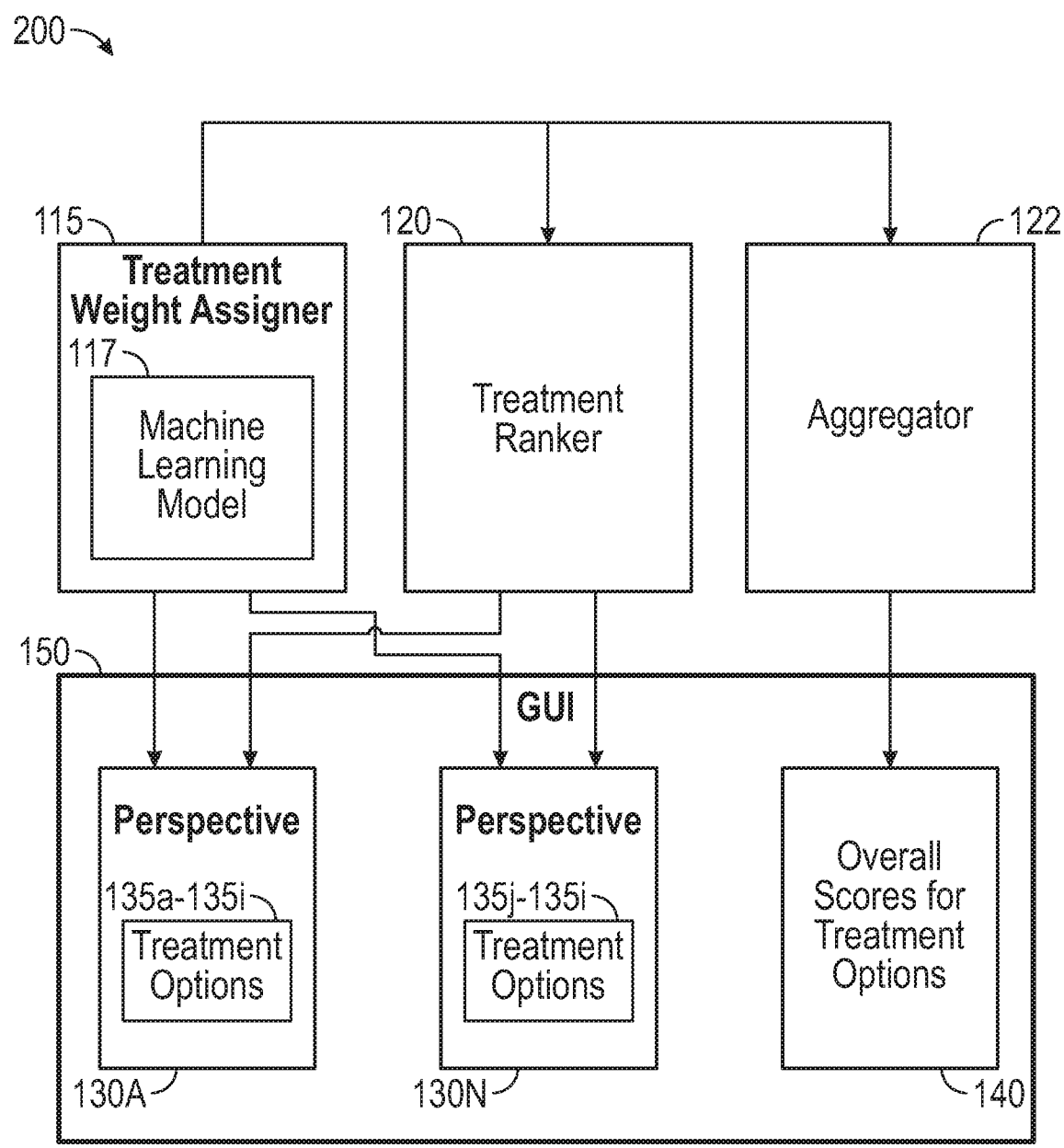
FIG. 2 illustrates a program architecture for providing an aggregate score for medical treatment options, according to one embodiment described herein.

FIG. 2 illustrates a program architecture 200 for providing an aggregate score for medical treatment options, according to one embodiment described herein. The treatment weight assigner 115 receives a plurality of medical perspectives (130a-130n) for each medical treatment option (e.g., 135i) of a plurality of medical treatment options (135a-135n) for a medical disorder. Each of the plurality of medical perspectives (130a-130n) provides an independent view for evaluating the plurality of medical treatment options (135a-135n) for treating the medical disorder. A medical perspective originates from one of a medical treatment guideline, a practice of an institutional, a computer-provided recommendation based on a review of relevant literature, a number of reported adverse effects for each medical treatment option in the medical perspective, and a cost of the medical treatment option.

The machine learning model 117 of the treatment weight assigner 115 assigns a weight to each of the plurality of medical perspectives (130a-130n) for each of the plurality of medical treatment options (135a-135n) by determining how often a care provider agrees with the plurality of medical perspectives (130a-130n) based on historical medical treatment option selections made by the care provider. Each weight is reflective of a preference for each of the plurality of medical perspectives 130a-130n by the care provider. The treatment weight assigner 115 assigns higher weights to medical treatment options (135a-135n) for medical perspectives 130a-130n that the care provider relies on and lower weights to medical treatment options (135a-135n) for medical perspectives 130a-130n that the care provider rarely uses. For example, the health care provider may place emphasis on two or three medical perspectives. The health care provider may agree with the institution ranking of medical treatment options. The healthcare provider may be very interested in whether or not the treatment is reimbursed by insurance, and may be interested in medical treatment options that have the least amount of adverse effects.

The treatment ranker 120 receives a medical treatment option ranking for each of the plurality of medical perspectives 130a-130n. Each ranking is based on how a corresponding one of the plurality of medical perspectives 130a-130n grades each of the plurality of the medical perspectives 130a-130n for each medical treatment option (e.g., 135i) of the plurality of medical treatment options (135a-135n).

The treatment ranker 120 generates a score for each medical perspective (e.g., 130i) of the plurality of medical perspectives 130a-130n as applied to each medical treatment option (e.g., 135i) of the plurality of medical treatment options (135a-135n) based on a combination of the weight and the ranking for each medical perspective (e.g., 130i). In an embodiment, generating a score for each medical perspective (e.g., 130i) comprises normalizing the ranking for each medical perspective (130a-130n).

The aggregator 122 aggregates the scores across the plurality of medical perspectives 130a-130n into an overall score for each of the plurality of medical treatment options (135a-135n) independent of the plurality of medical perspectives 130a-130n. In an embodiment, aggregating the scores across the plurality of medical perspectives (130a-130n) into an overall score includes multiplying the normalized ranking with a corresponding weight to arrive at a first score for a respective medical treatment option (e.g., 135i) and for a respective medical perspective (e.g., 130i). Aggregating the scores further includes averaging the first scores of all of the medical perspectives (130a-130i) for a respective medical treatment option (e.g., 135i) to arrive at the aggregated score for the respective medical treatment option (e.g., 135i). Aggregated scores for medical treatment options (135a-135n) are reflective of levels of confidence in the respective medical treatment options (135a-135n). Aggregate scores are intended to reflect a correlation between or a combination of the individual medical perspectives (130a-130n), but with an emphasis on medical perspectives favored by the health care provider. Accordingly, the aggregate scores are customized to a specific health care provider and their practice.

The aggregator 122 displays in the GUI 150 each medical treatment option (135a) based on the overall score for the medical treatment option (135a). In one embodiment, the aggregator 122 displays in the GUI 150 the aggregated scores for the plurality of medical treatment options (135a-135n).

In another embodiment, the aggregator 122 presents each medical treatment option (135a-135n) in order of overall score 140 for a respective medical treatment option (135a-135n) in the GUI 150 without displaying the overall score 140. In an embodiment, the computer system 100 can modify the GUI 150 based on an input from the care provider to alter the overall score of a medical treatment option currently displayed in the GUI 150. In an embodiment, the computer system 100 can modify the GUI (150) to prioritize medical perspectives based on preferences of the care provider.

In an embodiment, the computer system 100 can modify the GUI 150 based on the plurality of weights by identifying a preferred medical perspective (e.g., 130i) based on the plurality of weights and relocating the preferred medical perspective (e.g., 130i) to a more prominent position in the GUI 150, as compared to a second medical perspective (e.g., 130n) of the plurality of medical perspectives (130a-130n).

In an embodiment, the computer system 100 can further modify the GUI 150 based on the plurality of weights by the computer processor 100, upon determining that a weight associated with a third medical perspective of the plurality of medical perspective is below a predefined threshold, remove the third medical perspective from the GUI 150.

FIGS. 3A-3H show one example of a sequence that lead to providing an aggregate score for medical treatment options (135a-135n). FIG. 3A shows a set of medical treatment options (135a-135n) applicable to a patient in a leftmost column followed by a column each of recommendations (302a-302z) for the medical treatment options (135a-135n) on a per medical perspective basis (130a-130n). FIG. 3A shows no rankings or weighting of the medical treatment options (135a-135n). The medical treatment options (135a-135n) have been sorted alphabetically (i.e., medical perspectives (130a-130n) do not influence the order in which the medical treatment options (135a-135n) are displayed). The columns of medical perspective data (302a-302z) appear in a default order. Not all medical perspectives (130a-130n) need to provide a viewpoint (302a-302z) on all medical treatment options (135a-135n). The consensus guidelines (130b) do not mentioned the treatment cisplatin/gemcitabine so an entry (302i) for this is left blank. Column 2 shows the medical perspective (130a) of a single cancer treating institution. The medical perspective (130a) in column 2 indicates whether the treatments are preferred, acceptable, or not recommended. Column 3 shows the medical perspective (130b) from published guidelines representing a consensus from a variety of cancer treating institutions. The medical perspective (130b) in Column 3 indicates either uniform consensus backed by high-level supportive evidence or uniform consensus backed by low-level supportive evidence. Column 4 shows a medical perspective (130c) based on an evidence search, which indicates the number of articles found about the treatment given attributes that were entered. Column 5 shows a medical perspective (130d) based on adverse reactions. Column 6 is a medical perspective (130n) showing the relative cost of the given treatment.

FIG. 3B shows a set of attributes (304a-304z) of the medical treatment options (135a-135n) that each of the medical perspectives (130a-130n) of columns 2-6 from FIG. 3A rely upon to provide a recommendation (e.g., 302a) for a medical treatment option (e.g., 135a) followed by a column each of attributes (304a-304z) for the medical treatment options (135a-135n) on a per medical perspective basis.

FIG. 3C shows a listing (306a-306n) for each medical perspective (130a-130n) of the percentage of times a specific health care provider is in agreement with the respective medical perspectives of Columns 2-6 of FIG. 3A as well as a ranking (308a-308n) of the magnitude of each percentage. Columns 2-6 are indicative how often the health care provider is in agreement with the recommendations (302a-302z) of the respective medical perspectives (130a-130n). In the example shown in FIG. 3C, the health care provider frequently follows the guidelines recommended by a specific institution (130a). The health care provider follows consensus based guidelines (130b) most of the time. The number of published literature papers (130c) does not matter to the health care provider. The health care provider is also not concerned with the number of adverse reactions (130d). The health care provider often discusses the cost of treatments (130n) with patients and uses this as a tie-breaker when there are equally good treatments available.

FIG. 3D shows the medical treatment options (135a-135n) of Column 1 of FIG. 3A as well as preliminary ranks (310a-310n) assigned to each recommendation (302a-302z) within the context of each medical perspective (130a-130n) individually of Columns 2-6 of FIG. 3A by a default treatment ranker. Ties have the same "rank". Institutional specific recommendations (105a) are preferred and have the highest ranking (1). The consensus guidelines (130b) set to "Uniform, high" have the highest ranking (1), while "Disagreement" has the lowest ranking (2). For published literature (130c)—more literature ranked higher (1) than less literature (5). For adverse reactions (130d)—Fewer reactions are ranked highest (1). More reactions are ranked lowest (8). For relative cost (130n)—less expensive treatments are ranked higher (1) than costly treatments (4).

FIG. 3E show calculations of scores (312a-312z) for each medical perspective (130a-130n) and for each medical treatment option (135a-135n). The first number in each of the entries for each of the columns represent a medical perspective ranking (314a-314z) that is based on how a corresponding one of the plurality of medical perspectives 130a-130n grades each of the plurality of the each medical treatment option (e.g., 135a) of the plurality of medical treatment options (135a-135n). A medical treatment option's medical perspective ranking (314a-314z) is converted to a percentage to normalize all the rankings. (1/rank)*100. The second number in each of the entries for each of the columns represents health care provider's agreement percentage (306a-306z) for the medical perspective of each column. The normalized rank (314a-314z) is combined or multiplied by the health care provider's agreement percentage (306a-306z) for the medical perspective. This calculation causes the medical perspectives that the health care provider agrees with most frequently to influence the scores (312a-312z) the most.

FIG. 3F averages the scores (312a-312z) for each treatment option (135a-135n) to provide an aggregate (overall) score (318a-318n) for a medical treatment option (135a-135n) across all medical perspectives (130a-130n). The cells of a row are summed and then divided by the number of columns. (e.g., 2970+3600+580+975+3050=11175; 11175/5=2235).

FIGS. 3G and 3H shows that if a health care provider's medical perspective agreement falls below a threshold (e.g., 50%), then these medical perspectives (e.g., 130d, 130n) may be omitted from the aggregate (overall) scores calculations (as indicated by the "greyed out" columns).

Figure 4:
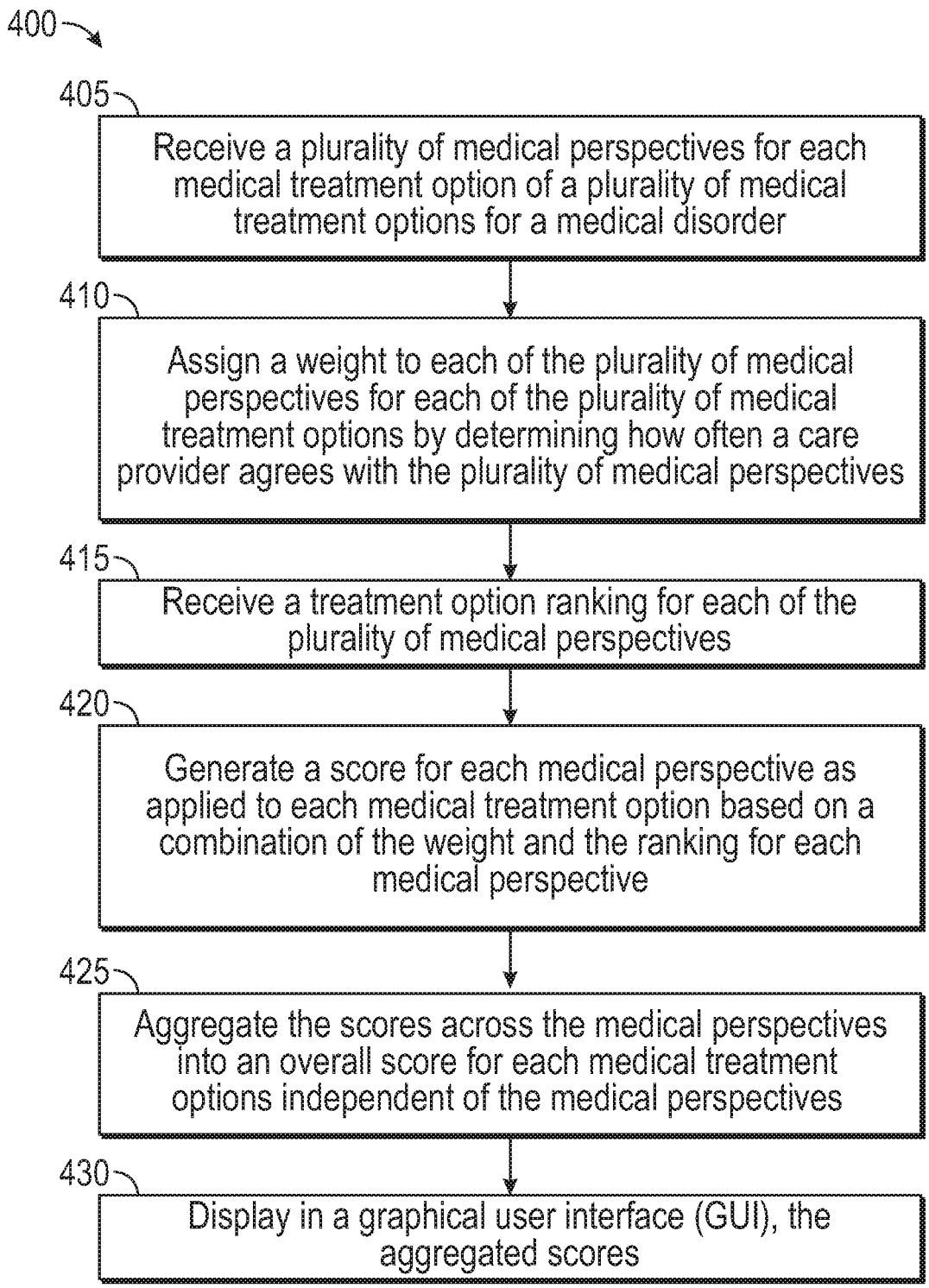
FIG. 4 illustrates one embodiment of a method for providing an aggregate score for medical treatment options.

FIG. 4 illustrates one embodiment of a method 400 for providing an aggregate score for medical treatment options. Method 400 can be performed by processing logic that can comprise hardware (e.g., circuitry, dedicated logic, programmable logic, microcode, etc.), software (e.g., instructions run on a processing device), or a combination thereof. In one embodiment, method 400 is performed by the treatment weight assigner 115, the treatment ranker 120, and the aggregator 122.

At block 405, the treatment weight assigner 115 receives a plurality of medical perspectives (130a-130n) for each medical treatment option (e.g., 135i) of a plurality of medical treatment options (135a-135n) for a medical disorder. Each of the plurality of medical perspectives (130a-130n) provides an independent view for evaluating the plurality of medical treatment options (135a-135n) for treating the medical disorder. A medical perspective originates from one of a medical treatment guideline, a practice of an institutional, a computer-provided recommendation based on a review of relevant literature, a number of reported adverse effects for each medical treatment option in the medical perspective, and a cost of the medical treatment option.

At block 410, the machine learning model 117 of the treatment weight assigner 115 assigns a weight to each of the plurality of medical perspectives (130a-130n) for each of the plurality of medical treatment options (135a-135n) by determining how often a care provider agrees with the plurality of medical perspectives (130a-130n) based on historical medical treatment option selections made by the care provider. Each weight is reflective of a preference for each of the plurality of medical perspectives 130a-130n by the care provider. The treatment weight assigner 115 assigns higher weights to medical treatment options for medical perspectives that the care provider relies on and lower weights to medical treatment options for medical perspectives that the care provider rarely uses.

At block 415, the treatment ranker 120 receives a medical treatment option ranking for each of the plurality of medical perspectives 130a-130n. Each ranking is based on how a corresponding one of the plurality of medical perspectives 130a-130n grades each of the plurality of the medical perspectives 130a-130n for each medical treatment option (e.g., 135i) of the plurality of medical treatment options (135a-135n).

At block 420, the treatment ranker 120 generates a score for each medical perspective (e.g., 130i) of the plurality of medical perspectives 130a-130n as applied to each medical treatment option (e.g., 135i) of the plurality of medical treatment options (135a-135n) based on a combination of the weight and the ranking for each medical perspective (e.g., 130i). In an embodiment, generating a score for each medical perspective (e.g., 130i) comprises normalizing the ranking for each medical perspective (130a-130n).

At block 425, the aggregator 122 aggregates the scores across the plurality of medical perspectives 130a-130n into an overall score for each of the plurality of medical treatment options (135a-135n) independent of the plurality of medical perspectives 130a-130n. In an embodiment, aggregating the scores across the plurality of medical perspectives (130a-130n) into an overall score includes multiplying the normalized ranking with a corresponding weight to arrive at a first score for a respective medical treatment option (e.g., 135i) and for a respective medical perspective (e.g., 130i). Aggregating the scores further includes averaging the first scores of all of the medical perspectives (130a-130i) for a respective medical treatment option (e.g., 135i) to arrive at the aggregated score for the respective medical treatment option (e.g., 318i). Aggregated scores for medical treatment options (135a-135n) are reflective of levels of confidence in the respective medical treatment options (135a-135n).

At block 430, the aggregator 122 displays in the GUI 150 each medical treatment option (135a) based on the overall score for the medical treatment option (135a). In one embodiment, the aggregator 122 displays in the GUI 150 the aggregated scores for the plurality of medical treatment options (135a-135n). In another embodiment, the aggregator 122 presents each medical treatment option (135a-135n) in order of overall score 140 for a respective medical treatment option (135a-135n) in the GUI 150 without displaying the overall score 140. In an embodiment, the aggregator 122 presents each medical treatment option (135a-135n) in order of overall score in the GUI 150 without showing the overall score. In an embodiment, the computer system 100 can modify the GUI 150 based on an input from the care provider to alter the overall score of a medical treatment option currently displayed in the GUI 150. In an embodiment, the computer system 100 can modify the GUI (150) to prioritize medical perspectives based on preferences of the care provider.

In an embodiment, the computer system 100 can modify the GUI 150 based on the plurality of weights by identifying a preferred medical perspective (e.g., 130i) based on the plurality of weights and relocating the preferred medical perspective (e.g., 130i) to a more prominent position in the GUI 150, as compared to a second medical perspective (e.g., 130n) of the plurality of medical perspectives (130a-130n).

In an embodiment, the computer system 100 can further modify the GUI 150 based on the plurality of weights by the computer processor 100, upon determining that a weight associated with a third medical perspective of the plurality of medical perspective is below a predefined threshold, remove the third medical perspective from the GUI 150.

Figure 5:
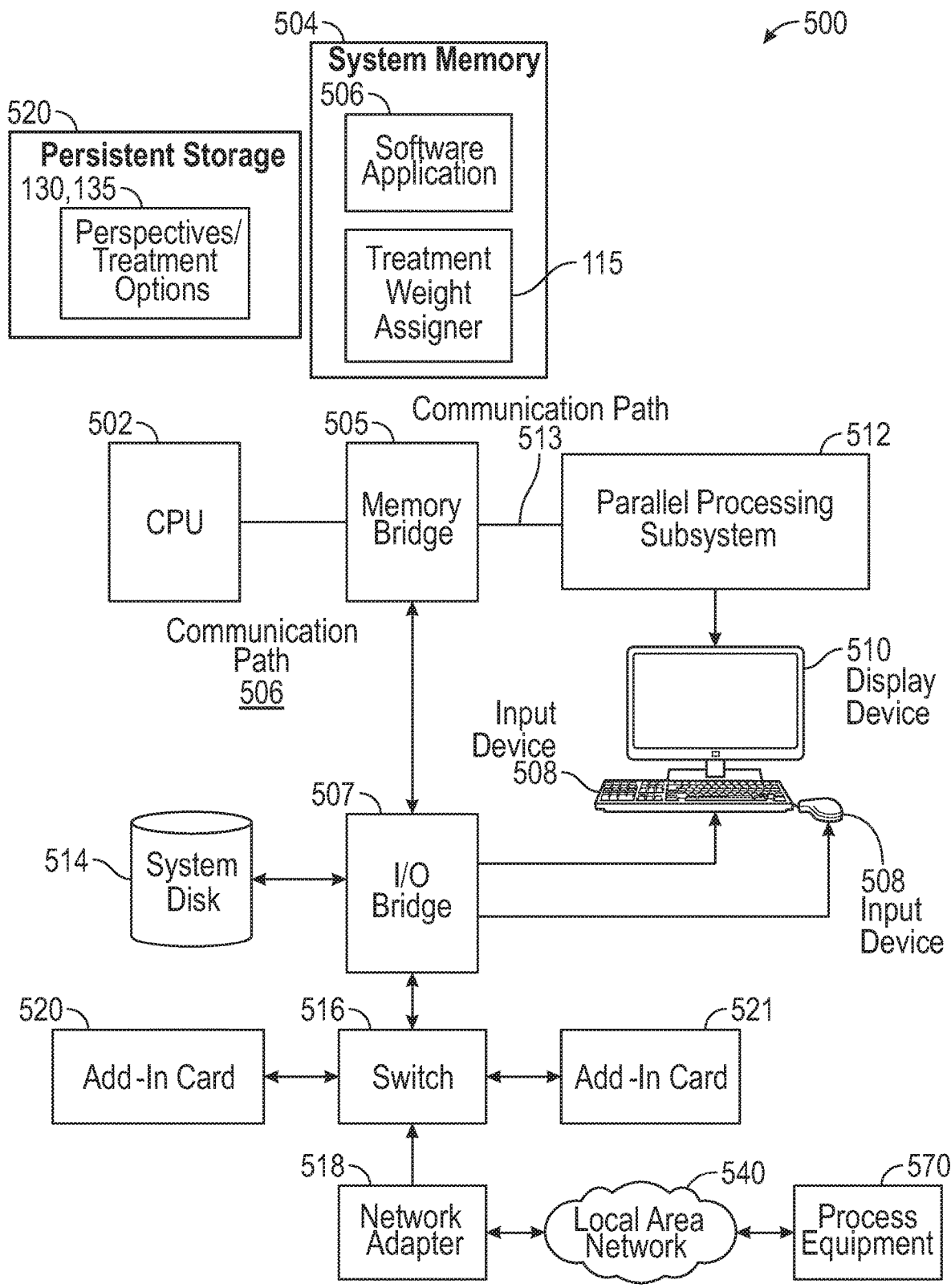
FIG. 5 illustrates an example computing system used for providing an aggregate score for medical treatment options, according to embodiments of the present disclosure.

FIG. 5 illustrates an example computing system used for providing an aggregate score for medical treatment options, according to embodiments of the present disclosure. In certain embodiments, computer system 500 is representative of the computer system 100. Aspects of computer system 500 may also be representative of other devices used to perform techniques described herein. For example, computing system 500 may be a personal computer, industrial processor, personal digital assistant, mobile phone, mobile device or any other device suitable for practicing one or more embodiments of the present invention.

The system 500 includes a central processing unit (CPU) 502 and a system memory 504 communicating via a bus path that may include a memory bridge 505. CPU 502 includes one or more processing cores, and, in operation, CPU 502 is the master processor of the system 500, controlling and coordinating operations of other system components. System memory 504 stores a software application 506, and data, for use by CPU 502. CPU 502 runs software applications and optionally an operating system. Illustratively, the system memory 504 includes the treatment weight assigner 115, the treatment ranker 120, and the aggregator 122, which perform operations related to provide an aggregate score for medical treatment options, according to techniques described herein.

Memory bridge 505, which may be, e.g., a Northbridge chip, is connected via a bus or other communication path (e.g., a HyperTransport link) to an I/O (input/output) bridge 507. I/O bridge 507, which may be, e.g., a Southbridge chip, receives user input from one or more user input devices 508 (e.g., keyboard, mouse, joystick, digitizer tablets, touch pads, touch screens, still or video cameras, motion sensors, and/or microphones) and forwards the input to CPU 502 via memory bridge 505.

A display processor 512 is coupled to the memory bridge 585 via a bus or other communication path (e.g., a PCI Express, Accelerated Graphics Port, or HyperTransport link); in one embodiment display processor 512 is a graphics subsystem that includes at least one graphics processing unit (GPU) and graphics memory. Graphics memory includes a display memory (e.g., a frame buffer) used for storing pixel data for each pixel of an output image. Graphics memory can be integrated in the same device as the GPU, connected as a separate device with the GPU, and/or implemented within system memory 504.

Display processor 512 periodically delivers pixels of the dashboard to a display device 510 (e.g., a screen or conventional CRT, plasma, OLED, SED or LCD based monitor or television). Additionally, display processor 512 may output pixels to film recorders adapted to reproduce computer 500 with an analog or digital signal.

Persistent storage 520 is also connected to I/O bridge 507 and may be configured to store content and applications and data, such as a database library 615, for use by CPU 502 and display processor 512. Persistent storage 520 provides non-volatile storage for applications and data and may include fixed or removable hard disk drives, flash memory devices, and CD-ROM, DVD-ROM, Blu-ray, HD-DVD, or other magnetic, optical, or solid state storage devices. Illustratively, persistent storage 520 includes medical treatment options 135 and medical perspective data 130.

A switch 516 provides connections between the I/O bridge 507 and other components such as a network adapter 518 and various add-in cards 520 and 521. Network adapter 518 allows the system 500 to communicate with other systems via an electronic communications network, and may include wired or wireless communication over local area networks 540 and wide area networks such as the Internet.

Other components (not shown), including USB or other port connections, film recording devices, or other suitable computing device, may also be connected to I/O bridge 507. For example, process equipment 570 may operate from instructions and/or data provided by CPU 502, system memory 504, or persistent storage 520. Communication paths interconnecting the various components in FIG. 5 may be implemented using any suitable protocols, such as PCI (Peripheral Component Interconnect), PCI Express (PCI-E), AGP (Accelerated Graphics Port), HyperTransport, or any other bus or point-to-point communication protocol(s), and connections between different devices may use different protocols, as is known in the art.

In one embodiment, display processor 512 incorporates circuitry optimized for performing mathematical operations, including, for example, math co-processor, and may additionally constitute a graphics processing unit (GPU). In another embodiment, display processor 512 incorporates circuitry optimized for general purpose processing. In yet another embodiment, display processor 512 may be integrated with one or more other system elements, such as the memory bridge 505, CPU 502, and I/O bridge 507 to form a system on chip (SoC). In still further embodiments, display processor 512 is omitted and software executed by CPU 502 performs the functions of display processor 512.

Pixel data can be provided to display processor 512 directly from CPU 502. In some embodiments, instructions and/or data representing a netlist incremental model verification is provided to set of server computers, each similar to the system 500, via network adapter 518 or system disk 514. The servers may perform operations on subsets of the data using the provided instructions for analysis. The results from these operations may be stored on computer-readable media in a digital format and optionally returned to the system 500 for further analysis or display. Similarly, data may be output to other systems for display, stored in a database library 515 on the system disk 514, or stored on computer-readable media in a digital format.

Alternatively, CPU 502 provides display processor 512 with data and/or instructions defining the desired output images, from which display processor 512 generates the pixel data of one or more output images, including characterizing and/or adjusting the offset between stereo image pairs. The data and/or instructions defining the desired output images can be stored in system memory 504 or graphics memory within display processor 512. CPU 502 and/or display processor 512 can employ any mathematical, function or technique known in the art to create one or more results from the provided data and instructions.

It will be appreciated that the system shown herein is illustrative and that variations and modifications are possible. The connection topology, including the number and arrangement of bridges, may be modified as desired. For instance, in some embodiments, system memory 504 is connected to CPU 502 directly rather than through a bridge, and other devices communicate with system memory 504 via memory bridge 505 and CPU 502. In other alternative topologies display processor 512 is connected to I/O bridge 507 or directly to CPU 502, rather than to memory bridge 505. In still other embodiments, I/O bridge 507 and memory bridge 505 might be integrated into a single chip. The particular components shown herein are optional; for instance, any number of add-in cards or peripheral devices might be supported. In some embodiments, the process equipment 570 may be connected directly to the I/O bridge 507. In some embodiments, the switch 516 is eliminated, and the network adapter 518 and the add-in cards 520, 521 connect directly to the I/O bridge 507.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

In the following, reference is made to embodiments presented in this disclosure. However, the scope of the present disclosure is not limited to specific described embodiments. Instead, any combination of the following features and elements, whether related to different embodiments or not, is contemplated to implement and practice contemplated embodiments. Furthermore, although embodiments disclosed herein may achieve advantages over other possible solutions or over the prior art, whether or not a particular advantage is achieved by a given embodiment is not limiting of the scope of the present disclosure. Thus, the following aspects, features, embodiments and advantages are merely illustrative and are not considered elements or limitations of the appended claims except where explicitly recited in a claim(s). Likewise, reference to "the invention" shall not be construed as a generalization of any inventive subject matter disclosed herein and shall not be considered to be an element or limitation of the appended claims except where explicitly recited in a claim(s).

Aspects of the present invention may take the form of an entirely hardware embodiment, an entirely software embodiment (including firmware, resident software, microcode, etc.) or an embodiment combining software and hardware aspects that may all generally be referred to herein as a "circuit," "module" or "system."

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and processor instructions.

Embodiments of the invention may be provided to end users through a cloud computing infrastructure. Cloud computing generally refers to the provision of scalable computing resources as a service over a network. More formally, cloud computing may be defined as a computing capability that provides an abstraction between the computing resource and its underlying technical architecture (e.g., servers, storage, networks), enabling convenient, on-demand network access to a shared pool of configurable computing resources that can be rapidly provisioned and released with minimal management effort or service provider interaction. Thus, cloud computing allows a user to access virtual computing resources (e.g., storage, data, applications, and even complete virtualized computing systems) in "the cloud," without regard for the underlying physical systems (or locations of those systems) used to provide the computing resources.

Typically, cloud computing resources are provided to a user on a pay-per-use basis, where users are charged only for the computing resources actually used (e.g. an amount of storage space consumed by a user or a number of virtualized systems instantiated by the user). A user can access any of the resources that reside in the cloud at any time, and from anywhere across the Internet. In context of the present invention, a user may access applications (e.g., the treatment weight assigner 115) or related data available in the cloud. For example, the treatment weight assigner 115 could execute on a computing system in the cloud. Doing so allows a user to access this information from any computing system attached to a network connected to the cloud (e.g., the Internet).

While the foregoing is directed to embodiments of the present invention, other and further embodiments of the invention may be devised without departing from the basic scope thereof, and the scope thereof is determined by the claims that follow.

What is claimed is:

1. A method for providing an aggregate score for medical treatment options, comprising:
   receiving a plurality of medical perspectives, wherein each of the plurality of medical perspectives provides an independent view for evaluating a plurality of medical treatment options for treating a medical disorder, wherein the plurality of medical perspectives comprise: (i) a treatment guideline perspective, (ii) an institutional practice perspective, (iii) a literature-based perspective, (iv) a perspective based on adverse events, and (v) a monetary cost perspective;
   assigning, by a machine learning model, a respective weight to each respective medical perspective of the plurality of medical perspectives, wherein the weights are specific to a first care provider, comprising:
      determining how often the first care provider agrees with each of the plurality of medical perspectives based on historical medical treatment option selections made by the first care provider;
      assigning a first weight to a first medical perspective of the plurality of medical perspectives based on determining a first percentage of times that the first care provider agrees with the first medical perspective based on historical medical treatment option selections made by the first care provider; and
      assigning a second weight to a second medical perspective of the plurality of medical perspectives based on determining a second percentage of times that the first care provider agrees with the second medical perspective based on historical medical treatment option selections made by the first care provider, wherein the second weight is lower than the first weight at least in part because the second percentage is lower than the first percentage;
   receiving a medical treatment option ranking for each of the plurality of medical perspectives, wherein each medical treatment option ranking is based on how a corresponding one of the plurality of medical perspectives grades each of the plurality of medical treatment options;
   generating a score for each medical perspective of the plurality of medical perspectives as applied to each medical treatment option of the plurality of medical treatment options based on a combination of the weight and the ranking for each medical perspective;
   aggregating the scores across the plurality of medical perspectives into an overall score for each of the plurality of medical treatment options independent of the plurality of medical perspectives; and
   displaying the overall scores in a graphical user interface (GUI), comprising:
      displaying each respective medical perspective of the plurality of medical perspectives in a respective column of the GUI;
      placing a highest-weighted medical perspective of the plurality of medical perspectives in a left-most column of the GUI, based on determining that the highest-weighted medical perspective is most preferred by the first care provider;
      placing a next highest-weighted medical perspective of the plurality of medical perspectives in a next open column of the GUI, based on determining that the next highest-weighted is not the most or least preferred by the first care provider; and
      removing the second medical perspective from the GUI, based on determining that the second medical perspective is not preferred by the first care provider and that the second weight is below a predefined threshold.

2. The method of claim 1, further comprising displaying, in a GUI, each medical treatment option based on the overall score for the medical treatment option.

3. The method of claim 2, wherein the GUI displays each medical treatment option in order of overall score in the GUI without showing the overall score of the medical treatment option.

4. The method of claim 2, further comprising modifying the GUI based on an input from the care provider to alter an overall score for a medical treatment option currently displayed in the GUI.

5. The method of claim 2, further comprising modifying the GUI to prioritize medical perspectives based on preferences of the care provider.

6. The method of claim 2, further comprising modifying the GUI based on the respective weights, comprising:
identifying a preferred medical perspective based on the respective weights; and
relocating the preferred medical perspective to a more prominent position in the GUI, as compared to a second medical perspective of the plurality of medical perspectives.

7. The method of claim 6, wherein modifying the GUI based on the plurality of weights further comprises:
upon determining that a weight associated with a third medical perspective of the plurality of medical perspective is below a predefined threshold, removing the third medical perspective from the GUI.

8. The method of claim 1, wherein generating a score for each medical perspective comprises normalizing the ranking for each medical perspectives.

9. The method of claim 8, wherein aggregating the scores across the plurality of medical perspectives into an overall score comprises:
multiplying the normalized ranking with a corresponding weight to arrive at a first score for a respective medical treatment option and for a respective medical perspective; and
averaging the first scores of all of the medical perspectives for a respective medical treatment option to arrive at the aggregated score for the respective medical treatment option.

10. The method of claim 1, further comprising assigning higher weights to medical treatment options for medical perspectives that the care provider relies on, and lower weights to medical treatment options for medical perspectives that the care provider rarely uses.

11. The method of claim 1, wherein overall scores for medical treatment options are reflective of levels of confidence in the respective medical treatment options.

12. A system, comprising:
a processor; and
a memory storing program code, which, when executed on the processor, performs operations for providing an aggregate score for medical treatment options, the operations comprising:
receiving a plurality of medical perspectives, wherein each of the plurality of medical perspectives provides an independent view for evaluating a plurality of medical treatment options for treating a medical disorder, wherein the plurality of medical perspectives comprise: (i) a treatment guideline perspective, (ii) an institutional practice perspective, (iii) a literature-based perspective, (iv) a perspective based on adverse events, and (v) a monetary cost perspective;
assigning, by a machine learning model, a respective weight to each respective medical perspective of the plurality of medical perspectives, wherein the weights are specific to a first care provider, comprising:
determining how often the first care provider agrees with each of the plurality of medical perspectives based on historical medical treatment option selections made by the first care provider;
assigning a first weight to a first medical perspective of the plurality of medical perspectives based on determining a first percentage of times that the first care provider agrees with the first medical perspective based on historical medical treatment option selections made by the first care provider; and
assigning a second weight to a second medical perspective of the plurality of medical perspectives based on determining a second percentage of times that the first care provider agrees with the second medical perspective based on historical medical treatment option selections made by the first care provider, wherein the second weight is lower than the first weight at least in part because the second percentage is lower than the first percentage;
receiving a medical treatment option ranking for each of the plurality of medical perspectives, wherein each medical treatment option ranking is based on how a corresponding one of the plurality of medical perspectives grades each of the plurality of medical treatment options;
generating a score for each medical perspective of the plurality of medical perspectives as applied to each medical treatment option of the plurality of medical treatment options based on a combination of the weight and the ranking for each medical perspective;
aggregating the scores across the plurality of medical perspectives into an overall score for each of the plurality of medical treatment options independent of the plurality of medical perspectives; and
displaying the overall scores in a graphical user interface (GUI), comprising:
displaying each respective medical perspective of the plurality of medical perspectives in a respective column of the GUI;
placing a highest-weighted medical perspective of the plurality of medical perspectives in a left-most column of the GUI, based on determining that the highest-weighted medical perspective is most preferred by the first care provider; and
placing a next highest-weighted medical perspective of the plurality of medical perspectives in a next open column of the GUI, based on determining that the next highest-weighted is not the most or least preferred by the first care provider; and
removing the second medical perspective from the GUI, based on determining that the second medical perspective is not preferred by the first care provider and that the second weight is below a predefined threshold.

13. The system of claim 12, further comprising displaying, in a GUI, each medical treatment option based on the overall score for the medical treatment option.

14. The system of claim 13, wherein the GUI displays each medical treatment option in order of overall score in the GUI without showing the overall score of the medical treatment option.

15. The system of claim 12, wherein generating a score for each medical perspective comprises normalizing the ranking for each medical perspective.

16. The system of claim 15, wherein aggregating the scores across the plurality of medical perspectives into an overall score comprises:

multiplying the normalized ranking with a corresponding weight to arrive at a first score for a respective medical treatment option and for a respective medical perspective; and averaging the first scores of all of the medical perspectives for a respective medical treatment option to arrive at the aggregated score for the respective medical treatment option.

17. A computer program product for, the computer program product comprising:

a computer-readable storage medium having computer-readable program code embodied therewith, the computer-readable program code executable by one or more computer processors to:

receive a plurality of medical perspectives, wherein each of the plurality of medical perspectives provides an independent view for evaluating a plurality of medical treatment options for treating a medical disorder, wherein the plurality of medical perspectives comprise: (i) a treatment guideline perspective, (ii) an institutional practice perspective, (iii) a literature-based perspective, (iv) a perspective based on adverse events, and (v) a monetary cost perspective;

assign, by a machine learning model, a respective weight to each respective medical perspective of the plurality of medical perspectives, wherein the weights are specific to a first care provider, comprising:

determining how often the first care provider agrees with each of the plurality of medical perspectives based on historical medical treatment option selections made by the first care provider;

assigning a first weight to a first medical perspective of the plurality of medical perspectives based on determining a first percentage of times that the first care provider agrees with the first medical perspective based on historical medical treatment option selections made by the first care provider; and assigning a second weight to a second medical perspective of the plurality of medical perspectives based on determining a second percentage of times that the first care provider agrees with the second medical perspective based on historical medical treatment option selections made by the first care provider, wherein the second weight is lower than the first weight at least in part because the second percentage is lower than the first percentage;

receive a medical treatment option ranking for each of the plurality of medical perspectives, wherein each medical treatment option ranking is based on how a corresponding one of the plurality of medical perspectives grades each of the plurality of medical treatment options;

generate a score for each medical perspective of the plurality of medical perspectives as applied to each medical treatment option of the plurality of medical treatment options based on a combination of the weight and the ranking for each medical perspective;

aggregate the scores across the plurality of medical perspectives into an overall score for each of the plurality of medical treatment options independent of the plurality of medical perspectives; and display the overall scores in a graphical user interface (GUI), comprising:

displaying each respective medical perspective of the plurality of medical perspectives in a respective column of the GUI;

placing a highest-weighted medical perspective of the plurality of medical perspectives in a left-most column of the GUI, based on determining that the highest-weighted medical perspective is most preferred by the first care provider;

placing a next highest-weighted medical perspective of the plurality of medical perspectives in a next open column of the GUI, based on determining that the next highest-weighted is not the most or least preferred by the first care provider; and removing the second medical perspective from the GUI, based on determining that the second medical perspective is not preferred by the first care provider and that the second weight is below a predefined threshold.

18. The computer program product of claim 17, wherein the computer-readable program code is further executable to display, in a GUI, each medical treatment option based on the overall score for the medical treatment option.

19. The computer program product of claim 18, wherein the GUI displays each medical treatment option in order of overall score in the GUI without showing the overall score of the medical treatment option.

20. The computer program product of claim 17, wherein the computer-readable program code is further executable to assign higher weights to medical treatment options for medical perspectives that the care provider relies on, and lower weights to medical treatment options for medical perspectives that the care provider rarely uses.

\* \* \* \* \*